United States Patent [19]

Mahoney et al.

[11] Patent Number: 5,925,009
[45] Date of Patent: Jul. 20, 1999

[54] ALGINATE FABRIC, METHOD OF PREPARATION AND USE

[75] Inventors: Peter M. J. Mahoney, Powys; David Kershaw, Gwent; David Pritchard, South Glamorgan; John Charles Fenton, Gwent, all of United Kingdom

[73] Assignee: Bristol-Myers Squibb Company, New York, N.Y.

[21] Appl. No.: 08/765,759

[22] PCT Filed: Jul. 5, 1995

[86] PCT No.: PCT/EP95/02541

§ 371 Date: May 30, 1997

§ 102(e) Date: May 30, 1997

[87] PCT Pub. No.: WO96/01658

PCT Pub. Date: Jan. 25, 1996

[30] Foreign Application Priority Data

Jul. 11, 1994 [GB] United Kingdom ............... 9413931

[51] Int. Cl.⁶ ........................................... A61L 15/00
[52] U.S. Cl. ................................... 602/44; 424/445
[58] Field of Search ............................. 602/44; 424/445

[56] References Cited

U.S. PATENT DOCUMENTS 5,470,576  11/1995  Patel ........................................ 424/445

FOREIGN PATENT DOCUMENTS 8039306  8/1980  United Kingdom .

*Primary Examiner*—Richard J. Apley
*Assistant Examiner*—Kelvin Hart
*Attorney, Agent, or Firm*—John M. Kilcoyne; Theodore R. Furman, Jr.

[57] ABSTRACT

Alginate fabrics have, in conjuction with charcoal cloth, been used in wound dressings for malodorous wounds and there are commercial examples of such wound dressings. A problem associated with known alginate wound dressings which employ charcoal cloth is that the dressing is a relatively rigid structure. Furthermore, the known dressings have been constrained to the use of charcoal cloth which limits the absorptive properties thereof for wound odorants due to the fixed surface area of the cloth. We have now developed an alginate fabric which alleviates the above problems, and there is provided by the present invention an alginate fabric having particulate charcoal dispersed therein.

15 Claims, 5 Drawing Sheets

ALGINATE FABRIC, METHOD OF PREPARATION AND USE

The present invention is concerned with an alginate fabric, and in particular the use thereof as a wound dressing and a method of preparing the same.

Alginate fibres have been known for some time as being useful in the preparation of alginate fabric wound dressings. A number of methods for producing conventional alginate fibres are described in the art. The extrusion of alginate solutions into an aqueous solution containing calcium ions to form calcium alginate filaments is known, for example, from British Patent Specifications Nos. 567641, 568177, 571657 and 624987. The replacement of a proportion of the calcium ions in calcium alginate by sodium ions to produce a more soluble fibre is known from British Patent Specification No. 653341.

Alginate fabrics have, in conjunction with charcoal cloth, been used in wound dressings for malodorous wounds and examples of such commercially available wound dressings are sold under the trademarks KALTOCARB, ACTISORB and LYOFOAM. A dressing available under the trade mark KALTOCARB comprises a non-woven alginate pad and charcoal cloth fused together with a polyamide net; a dressing available under the trade mark ACTISORB comprises charcoal cloth together with silver sealed within a nylon sleeve and may further include one or more absorbent layers; a dressing available under the trade mark LYOFOAM includes viscose fibres treated with activated charcoal encapsulated by a layer of polyurethane foam.

EP 0099758 also describes a composite wound dressing which can include alginate fabric used in conjunction with charcoal cloth. The wound dressing of EP 0099758 comprises a semipermeable membrane, which may comprise an alginate, a supporting layer such as charcoal cloth and a biodegradable tissue interface such as sodium-calcium alginate. The supporting layer is located between the semipermeable membrane and the biodegradable tissue interface.

A problem associated with known alginate wound dressings which employ charcoal cloth is that the dressing is a relatively rigid structure. Furthermore, the known dressings have been constrained to the use of charcoal cloth which limits the absorptive properties thereof for wound odourants due to the fixed surface area of the cloth. The above is due to the hitherto inability to incorporate charcoal within the alginate fabric, and the use of certain types of charcoal, such as powder, granules or the like, has therefore been excluded from alginate fabric wound dressings.

We have now developed an alginate fabric which alleviates the above problems, and there is provided by the present invention an alginate fabric having particulate charcoal dispersed therein.

There is further provided by the present invention a wound dressing comprising an alginate fabric, the fabric having particulate charcoal dispersed therein. Typically the fabric employed in a wound dressing according to the present invention is 0.5 to 5 mm thick.

The charcoal can be in the form of powder, granules and the like. Suitably powdered charcoal is employed in fabric according to the present invention, as this provides an increased surface area for absorption of odourants from malodorous wounds. Aptly the charcoal employed in the present invention has a surface area of 500 to 3000 $m^2/g$, more aptly 1500 to 2500 $m^2/g$ and most aptly 1800 to 2200 $m^2/g$.

Typically the charcoal is present in the alginate fabric in an amount of 1 to 30% by weight, based on the weight of the fabric. More suitably however the charcoal is present in an amount of 10 to 20% by weight, based on the weight of the fabric.

The alginate fabric of the present invention desirably comprises alginate fibres which are very much more absorbent than conventional alginate fibres. This is a considerable advantage for use in environments where high absorption coupled with biodegradability is desired, for example in wound dressings such as dressings for ulcers or burns. The high rate of absorption achieved with such fibres employed in alginate fabrics of this invention is a further advantage, particularly for use in dressings.

The fibres employed in fabric according to the invention may be characterised by reference to their unique thermal properties, in that a plot of the first order derivative of percentage weight loss of the fibre with temperature against temperature has two maxima in the range of 100 to 400° C.

In general, the two maxima in the plot of the first order derivative of percentage weight loss with temperature against temperature for a fibre according to the invention will fall within the range 200 to 300° C., preferably 220 to 290° C.

Thermogravimetric analysis was performed using a 2950TGA manufactured by TA Instruments, Delaware, U.S.A. Differential scanning calorimetry (DSC) was performed using a DSC7manufactured by Perkin-Elmer.

Figure 1:
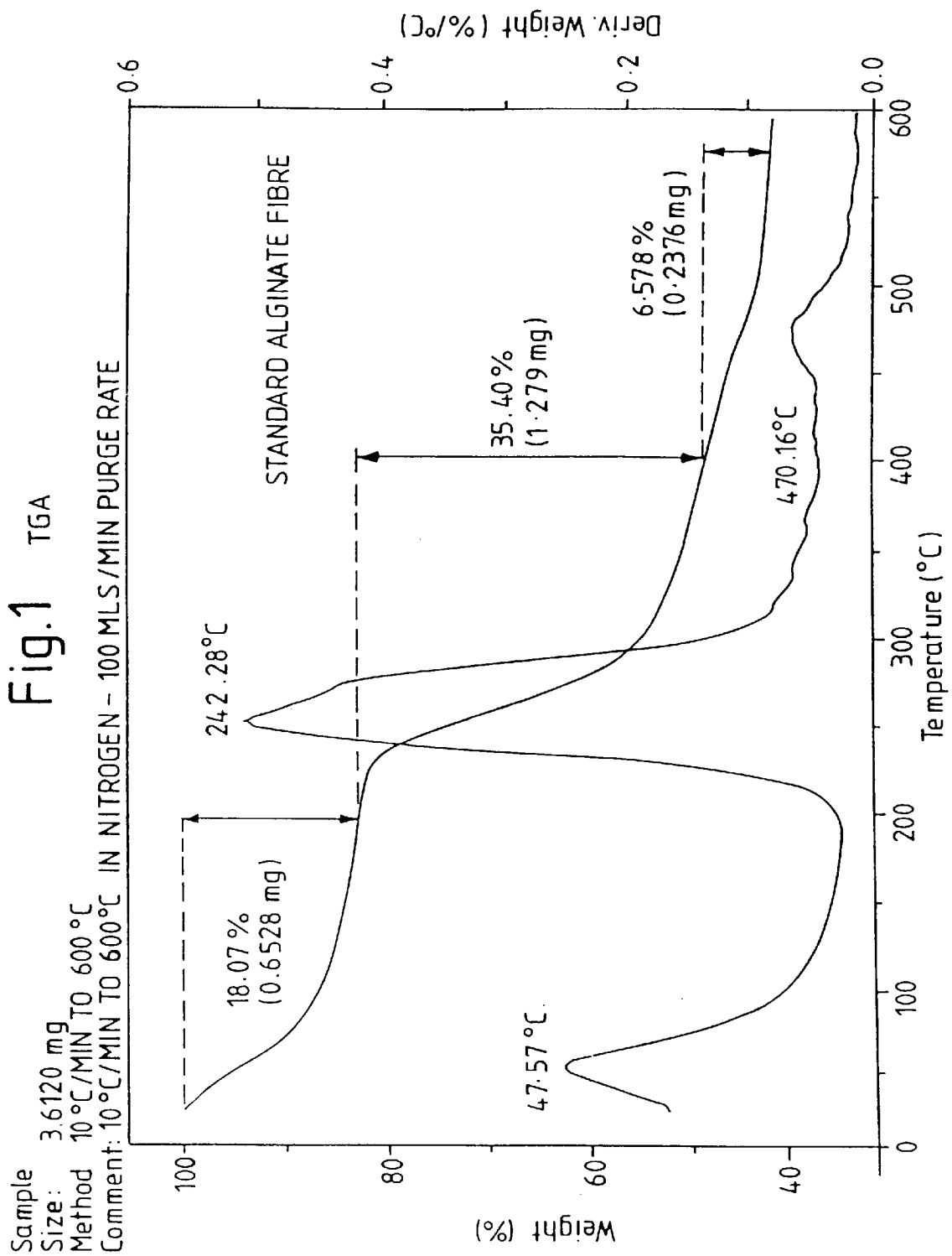
FIG. 1 shows the thermogravimetric analysis (TGA) of an 80:20 calcium:sodium alginate fibre prepared by conventional methods.
Figure 2:
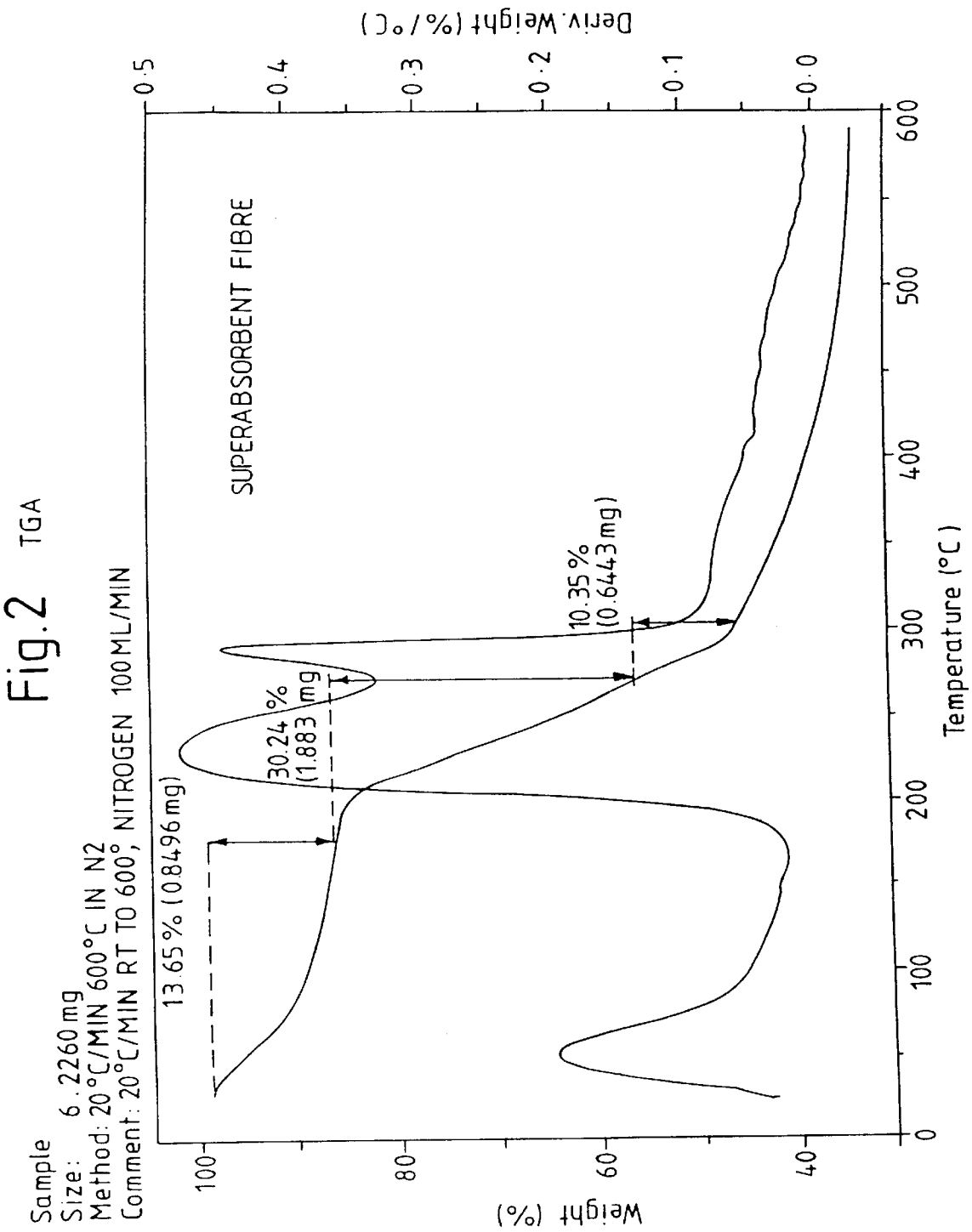
FIG. 2 shows the thermogravimetric analysis (TGA) of a fibre employed according to the invention, prepared from the same source material as the fibre of FIG. 1.

FIG. 1 shows the percentage weight loss of a conventional alginate fibre with increasing temperature, and the first order derivative of that function. The derivative shows a single maximum at approximately 240° C. In contrast, the first order derivative of percentage weight loss with temperature for a corresponding fibre employed according to the present invention, shown in FIG. 2, has two peaks, one at a lower temperature than the maximum observed for the conventional fibre (approximately 225° C.), and one at a higher temperature than the maximum observed for the conventional fibre (approximately 280° C.). This "splitting" of the derivative maximum for the conventional fibre of the same composition is characteristic of fibres employed according to the present invention.

Figure 3:
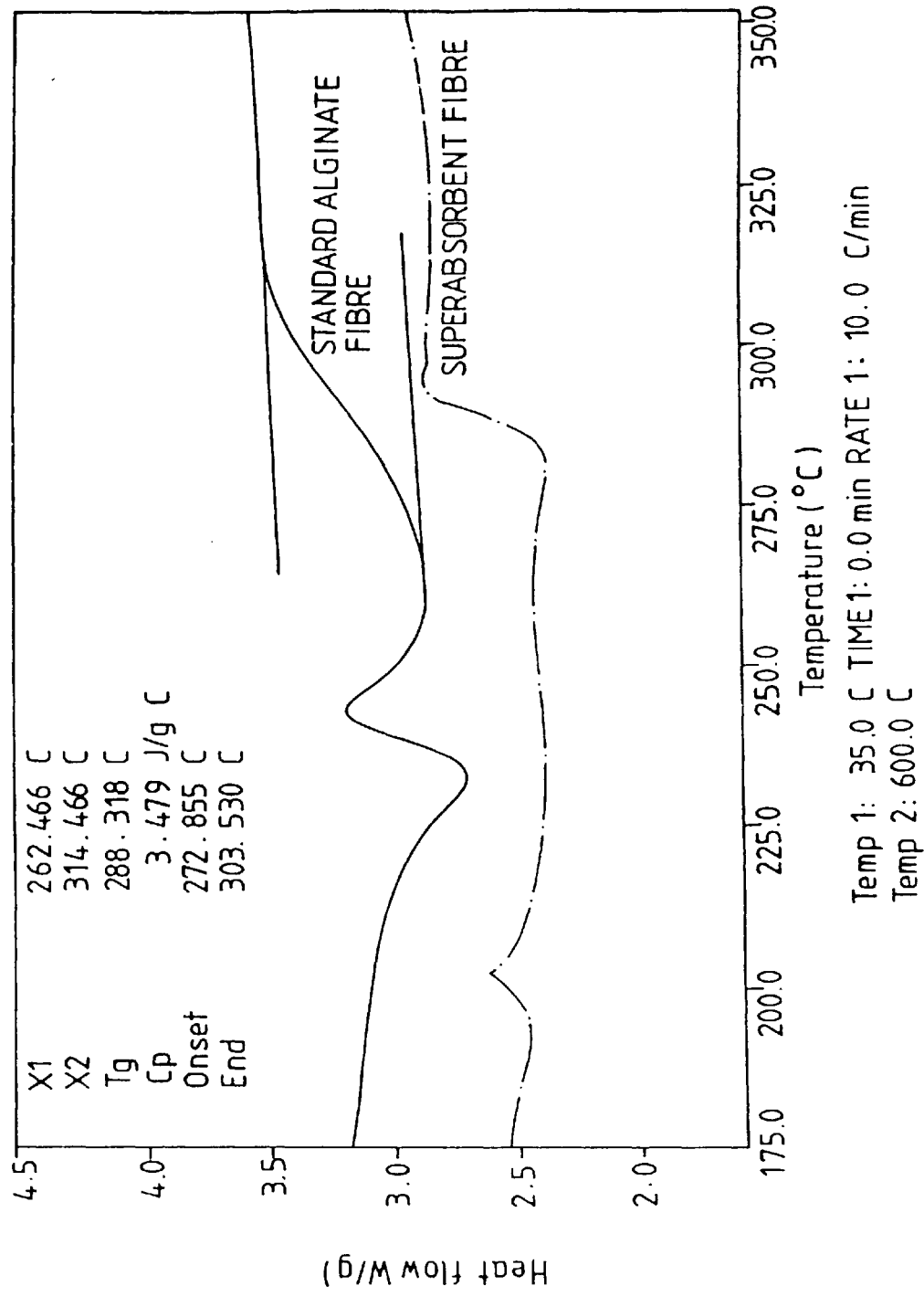
FIG. 3 shows the variation of heat flow with temperature for a conventional 80:20 calcium:sodium alginate fibre and a corresponding fibre employed in accordance with the present invention.
Figure 4:
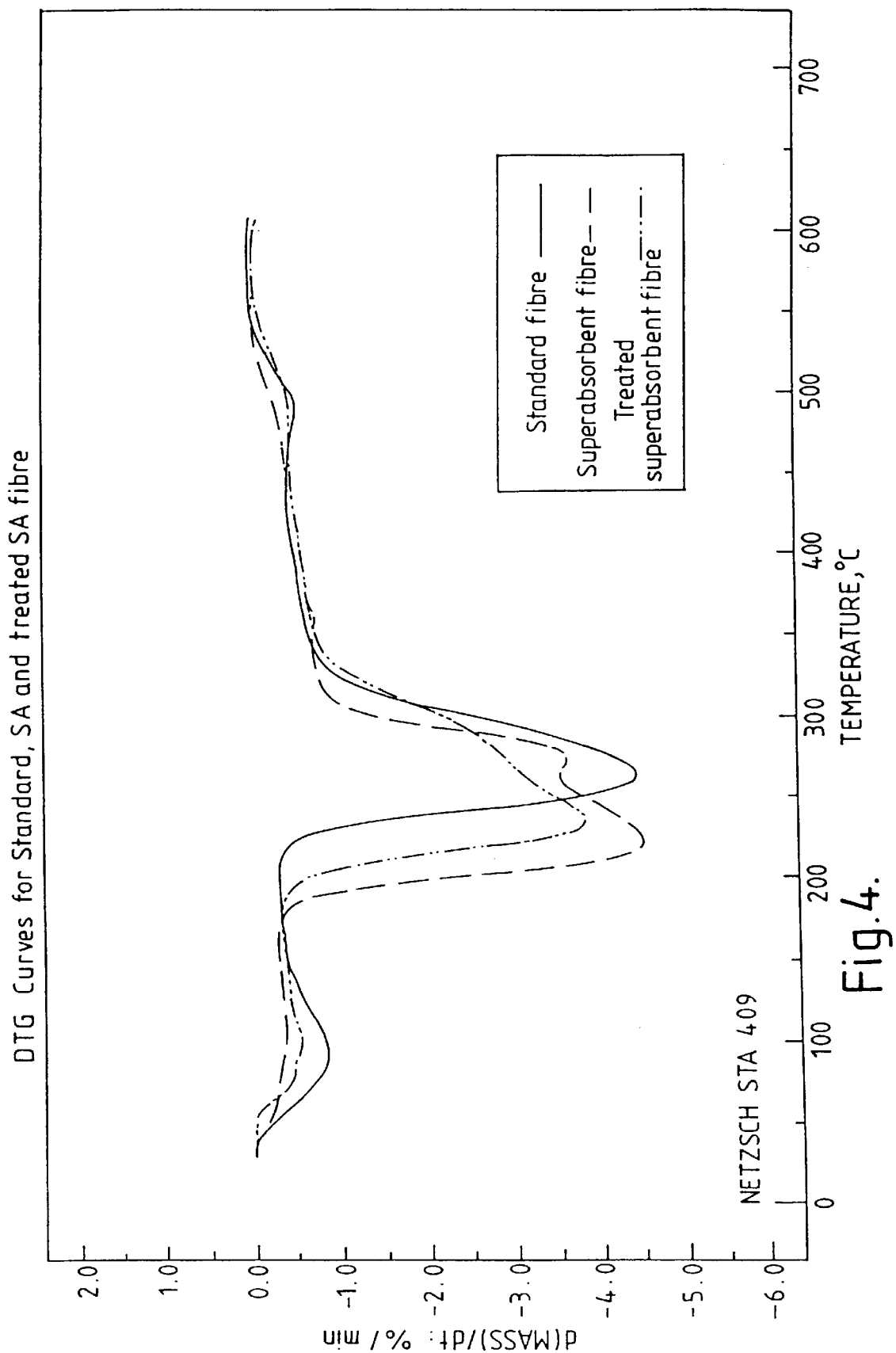
FIG. 4 shows the thermogravimetric analysis of a conventional fibre, a high absorbency fibre employed according to this invention and such a fibre treated with calcium ions.

FIG. 3 also shows differences in the thermal properties of a conventional alginate fibre and a fibre employed according to the present invention. Heat flow is effectively a measure of enthalpy associated with a transition, reaction or decomposition. The glass transition temperature (Tg) shown in FIG. 3 is the same for both fibres (288° C.). However, it can be seen that the transition for the conventional fibre is broad, occurring over some 50° C., whereas that for the fibre employed in accordance with the invention is sharp, taking place over less than 20° C.

Alginate fibres employed in fabrics according to the present invention can further be characterised in terms of their glass transition temperature, and in a further or alternative aspect, the present invention thus provides an alginate fabric having particulate charcoal dispersed therein, wherein the fabric comprises alginate fibre having a glass transition temperature of less than 30° C., such as about 26° C.

Alginate fibres employed in fabrics according to the present invention can further be characterised in terms of their dielectric behaviour. For polymers the dielectric constant is dependent on the ease with which the polymer orientates itself in response to an applied field and this is a function of the structure of the polymer. The constant is most easily expressed in terms of the relationship between the in-phase and out-of-chase components of the dynamic field. This is conventionally expressed as Tan δ. Multiple peaks are normally recorded when measuring Tan δ due to a variety of relaxation phenomena. We have found that alginate fibres suitable for use in the fabrics of the present invention have Tan δ values in the range of less than 1 and up to 15 Hz. Conventional alginate fibres have Tan δ values of from 40 Hz to 7000 Hz.

Figure 5:
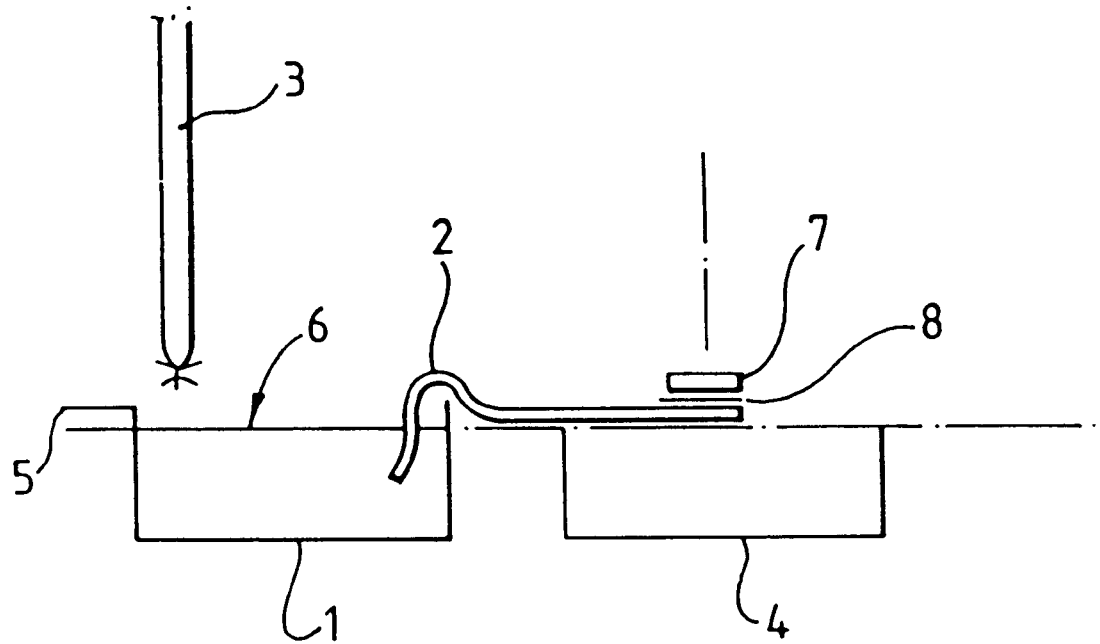
FIG. 5 shows apparatus suitable for determining absorbency.

As hereinbefore described alginate fibres employed in fabrics of the present invention exhibit improved absorptive properties and the present invention accordingly provides an alginate fabric having particulate charcoal dispersed therein, wherein the absorbency of the fabric may be at least 40.0 grams of deionised water per gram of fabric as measured with reference to a test method depicted in FIG. 5 appended hereto.

Alginate fabric employed in the present invention aptly has an absorbency of at least 40 times its own weight of deionised water and more aptly at least 60 times and most aptly at least 80 times its own weight of deionised water. Typically the fabric has an absorbency of much greater than this, for example 80 to 280 times its own weight, such as about 120 grams of deionised water per gram of fabric.

Alginate fibres suitable for preparing a fabric according to the present invention, are typically obtained by a process comprising the following steps:

(1) treating alginate fibres with a suitable acid so as to produce fibres comprising approximately 90–98%, such as 95%–98%, alginic acid fibres;

(2) treating the alginic acid fibres with a saturated aqueous solution of mono- or divalent cations;

(3) washing the fibres with water until imbibition of water by the fibres has effectively ceased;

(4) treating the fibres with a source of a cation capable of forming a water-soluble alginate salt.

The present invention also provides an alginate fabric having particulate charcoal dispersed therein, the fabric comprising alginate fibres prepared according to the above described process.

The fibres used as starting material in step 1 may be conventional salted alginate fibres (for example sodium, calcium, mixed sodium/calcium fibres produced in conventional manner, for example from 2–10% w/w solutions, for example 4% solution)

Most suitably the alginate fibres for use in step (1) are calcium alginate fibres which are spun from a 2 to 8% sodium alginate dope solution by weight, preferably 4 to 6% sodium alginate solution, employing techniques conventional to the art.

Suitable acids for use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations for use in step (2) include solutions of sodium, potassium and magnesium cations. Preferably a pharmaceutically acceptable monovalent cation is used, most preferably a sodium ion.

Step (3) is preferably effected by washing the fibres in a stream of deionised water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for example by treatment with a volatile drying agent, such as methyl alcohol, ethyl alcohol, isopropyl alcohol, acetone and the like, and then drying in air. It is one of the advantages of this invention that the highly absorbent fibres may be dried without losing their ability to be highly absorbent when rewetted.

For the most highly absorbent products to be obtained, large amounts of divalent ions such as calcium ions are not added at step (4) or later.

The alginate may be obtained from any convenient source, for example L. Hyperbola or Eclomia Maxima of which Eclonia Maxima is preferred.

The fibres prepared according to the above described process may be dried using conventional methods, for example, using acetone or hot air drying.

In order to prepare an alginate fabric according to the present invention, particulate charcoal substantially as hereinbefore described, together with the abovementioned high absorbency alginate fibres, are suspended in deionised water and stirred for about 10 to 30 minutes, typically 15 to 25 minutes. The alginate fibres absorb the water, and a slurry is achieved. The use of such high absorbency alginate fibres in the preparation of alginate fabrics according to the present invention is therefore advantageous in achieving dispersal of the particulate charcoal in the above described slurry. Conventional alginate fibres do not absorb water in this way, and it has not hitherto been possible to achieve a slurry of the alginate in which particulate charcoal can be dispersed.

The resultant slurry of the alginate, together with the dispersed particulate charcoal, is subsequently dried, typically by filtration under vacuum, or other suitable method, and optionally by treatment with a volatile drying agent such as methyl alcohol, ethyl alcohol, isopropyl alcohol, acetone and the like substantially as hereinbefore described.

A pad of an alginate fabric having particulate charcoal dispersed therein is obtained, and the pad can be modified so as to vary the absorbency of the fibres to be employed in the resultant alginate fabric according to the present invention. For example, the fibres may be treated with an aqueous solution of a desired ion, for example if it is desired to increase the calcium ion content treatment with a source of calcium ions such as a solution of a calcium salt, such as calcium chloride, calcium sulphate and the like may be used. Suitably calcium chloride is employed.

Suitably the treated alginate fibres and charcoal may be further dried under vacuum to remove any remaining drying agent. The resultant alginate fabric containing the dispersed charcoal is further dried in an oven to a constant weight, typically at a temperature in the range of 40–60° C., aptly 45–55° C.

Alginate fabrics according to the present invention may have medicaments incorporated therein. Suitable medicaments include those which aid recovery of wounds, for example an antifungal agent, an antibacterial agent, an angiogenesis promoting agent or the like. Favoured medicaments include antifungal agents such as metronidazole, and antibacterial agents such as chlorhexidine, prepared by treating the fibres with an aqueous solution of the medicament or its salt.

It has further been found that hyaluronic acid can be incorporated into the alginate fibres of the fabrics according to the present invention.

Hyaluronic acid (hereinafter referred to as HA) is a natural high viscosity mucopolysaccharide, generally having a molecular weight range of $3 \times 10^3$ to $8 \times 10^6$ Daltons (although there are reports of HA having molecular weights as high as $13 \times 10^6$) depending on source, method of isolation and method of determination. The isolation and characterisation of HA are described in Meyer, et al., J. Biol. Chem. 107, 629, (1934); J. Biol. Chem. 114, 689, (1936); Balazs, Fed. Proc. 17, 1086, (1958); Laurent, et al., Biochem. Biophys. Acta. 42, 476, (1960); Weissman, et al., J. Am. Chem. Soc., 76, 1753, (1954); and Meyer, Fed. Proc. 17, 1075, (1958).

HA is normally employed as its sodium salt although some other salting ions such as potassium or calcium or the like may also be present. All such physiologically acceptable forms and especially the sodium salt are encompassed within the term HA herein.

HA is frequently used in ocular surgery as a replacement for subretinal fluid and vitreous humour. HA can also be used as a replacement for synovial fluid that is lost as a result of surgery or chronic inflammatory disease such as rheumatoid arthritis. HA is also known to be implicated in wound healing and angiogenesis. A wound dressing capable of providing sustained release of hyaluronic acid might therefore be expected to promote wound healing and/or angiogenesis.

A suitable average molecular weight range for HA for use in the fibres of the present invention is $1.5 \times 10^3$ to $2 \times 10^6$, such as $1 \times 10^4$ to $1 \times 10^6$, preferably $1.5 \times 10^4$ to $1 \times 10^5$, more preferably about $7.5 \times 10^4$.

It is believed that the HA incorporated into fibres of the alginate fabric of the invention resides in spaces or "pockets" in the internal structure of the fibre and that release of the HA from the fibre to the environment of use takes place in a sustained manner as the fibre swells under the conditions of use. For example, high absorbency fibres as hereinbefore described containing HA may be formed into a fabric used to prepare a wound dressing. As the dressing absorbs wound exudate, the fibres swell and HA is delivered to the wound in a sustained manner.

Incorporation of HA into the alginate fibres may be achieved by contacting alginate fibres with an aqueous solution of HA followed by a suitable aqueous ionic solution, such as a solution of calcium, magnesium or zinc cations, preferably a solution of calcium cations, more preferably aqueous calcium chloride solution.

As hereinbefore the alginate fabric according to the present invention is particularly suitable for use as a wound dressing.

A wound dressing according to the present invention may also comprise one or more further absorbent layers. Suitably a further absorbent layer is arrangable facing the wound so as to obviate shedding of particulate material, such as the charcoal dispersed in the alginate fabric according to the invention, into a wound. The wound dressing may include one or more absorbent layers arranged on either side of an alginate fabric according to the present invention.

Suitably the absorbent layer or layers is selected from the group consisting of alginate fibres, karaya gum, locust bean gum, guar gum, sodium acrylate, polyvinyl alcohol, pectin, gelatin, carboxymethylcellulose, high molecular weight carbowaxes, carboxy polymethyl collagen and cotton.

Aptly the absorbent layer comprises alginate fibres. Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units.

Suitably alginate fibres employed in the absorbent layer may be high M or high G, typically 60–80% by weight M or G respectively. The alginate fibres may be high absorbent fibres substantially as hereinbefore described.

The alginate fibres of the further absorbent layer or layers may, for example, be non-woven, woven or knitted. Preferably, the fabric is non-woven, not only from the standpoint of ease of manufacture but also because of the general dimensional stability of non-woven fabrics, which are acknowledged not to stretch so easily as, for example, knitted fabrics.

In the preparation of a non-woven fabric, a cotton card may be used to form a web, which may then be cross-lapped, for example with a Garnet Bywater cross-lapper, and then needle punched in a Garnet Bywater needle loom. In the preparation of a woven fabric, the precursor alginate fibres may be carded and then spun into a yarn, which can be woven in a conventional loom. Alternatively, the fibres may be collected in a spinning box, according to the method described in British Patent No. 568177, and woven. In the preparation of a knitted fabric, the fibres can be prepared as a continuous filament yarn, again according to the method described in British Patent No. 568177, which is then knitted on a conventional knitting machine.

The wound dressing according to the present invention may further be provided with an occlusive film, suitable films comprising a polyurethane, polyethylene, polypropylene, polyether/polyester derivatives and the like.

The wound dressings formed from the alginate fabric according to the present invention will advantageously be conventional dressings well known in the art. Examples of suitable dressings include bandages, adhesive strip dressings, island dressings, pads of various kinds, surgical sponges and packs and ward dressings. Such dressings may conveniently be prepared by standard methods known from the art.

The dressings in accordance with the present invention will conveniently be packaged in an hermetically-sealed envelope and sterilised, e.g. with ethylene oxide or by irradiation using gamma rays or an electron beam.

The absorbency of fabric according to the invention may be determined according to the following method.

TEST METHOD 1

The apparatus used in the determination of absorbency is depicted in FIG. 5, and consists of water bath 1 containing a 0.9% (w/w) aqueous saline solution, or deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 5. The balance 4 is then tared. A weighed dressing 7 and filter paper 8 (cut to size) is positioned as depicted in FIG. 5. Care must be taken to ensure that the edge of the absorbent strip 2 furthest away from the water bath 1 does not extend beyond the corresponding edge of the dressing 7, as shown in FIG. 5.

After six minutes the weight shown on the balance 4 is recorded. The dressing 7 and filter paper 8 are then removed and any residual weight on the balance 4 noted.

Absorbency is determined on the basis of the following equation:

$$\begin{matrix} \text{Weight} \\ \text{of} \\ \text{liquid} \\ \text{absorbed} \end{matrix} = \begin{matrix} \text{total} \\ \text{weight} \\ \text{on} \\ \text{balance} \end{matrix} - \left[ \begin{matrix} \text{dry} \\ \text{weight} \\ \text{of} \\ \text{dressing} \end{matrix} + \begin{matrix} \text{weight of} \\ \text{saturated} \\ \text{filter} \\ \text{paper} \end{matrix} + \begin{matrix} \text{residual} \\ \text{weight on} \\ \text{balance} \end{matrix} \right]$$

TEST METHOD 2

The Tan δ value of a fibre was determined by using a Thurlby Thandor TG502 sweep/function generator, a Tectronics 2212 digital storage oscilloscope and a capacitance test cell (plate area 16 square centimeters and fitted with a 22 KΩ resistor). The material to be tested was placed in a small engineers vice and the vice closed. The distance between the plates was measured using a vernier calliper and the earth connection made between the vice and the earth terminal of the capacitance test cell. The function generator and oscilloscope were then connected and the amplitude of the applied sinusoidal voltage measured together with the voltage drop across the resistor and the phase angle between the applied voltage signal and current. The frequency of the applied field was then altered and the measurements repeated for many points in the range 5 mHz to 5 MHZ.

The following non-limiting Examples are intended to illustrate the present invention.

EXAMPLE 1

Calcium alginate fibre was spun from a 4 to 6% by weight sodium alginate dope solution, and 4 g of the resulting fibre was immersed in 1M hydrochloric acid (1 1) for 20–30 seconds. The degree of acid conversion was determined from the relative intensities of the peaks at 1720 $cm^{-1}$ and 1600 $cm^{-1}$ in the infrared spectrum, to ensure that the degree of conversion was in excess of 95%. The fibre was then washed with water and immersed in saturated saline solution (2 1). The fibre was then chopped to the required staple length. After cutting to the appropriate length the fibre was dispersed into a stirred vessel containing deionised water (2 1). The fibres were washed in a stream of running water until they swelled to their maximum extent and no sodium chloride could be detected in the eluent. Sodium carbonate solution (0.1M) was then added in 1 ml aliquots whilst monitoring the pH and conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

0.4 g of the resultant fibres, together with 0.1 g of charcoal powder, were suspended in 50 $cm^3$ of deionised water and stirred for 20 minutes.

100 mesh nylon gauze disk was placed in the bottom of a 7 cm diameter Buchner funnel and placed on top of a Buchner flask attached to a vacuum pump. The alginate/charcoal suspension was poured into the funnel and the water allowed to drain from the resulting alginate/charcoal pad. A vacuum was applied to remove remaining water.

Approximately 30 ml of isopropyl alcohol was poured onto the pad and allowed to drain there through. A vacuum was then applied to remove the remaining solvent.

The pad was dried in an oven at 50° C. to constant weight.

EXAMPLE 2

A pressure sensitive adhesive (suitably available under the trade mark acronal V205, 70% solids aqueous dispersion) was applied to the surface of the pad obtained by Example 1 (4 ml per 10 cm×10 cm pad) and spread with a doctor knife to give a thin uniform layer.

The adhesive layer was then allowed to dry prior to being covered by a 10 cm×10 cm, 100 gsm further absorbent alginate pad comprising a commercially available calcium sodium alginate (suitably available under the trade mark KALTOSTAT).

EXAMPLE 3

A pressure sensitive adhesive (suitably available under the trade mark acronal V205, 70% solids aqueous dispersion) was applied to the pad obtained in Example 1 as described in Example 2.

The adhesive layer was then allowed to dry prior to being covered by a 10 cm×10 cm, 100 gsm further absorbent alginate pad again as described in Example 2.

The dressing was then turned over and a further alginate pad was applied to the opposed surface of the pad of Example 1 in a manner as described above.

EXAMPLE 4

A piece of tackified polyurethane film (0.2 μm thickness, 14 cm×14 cm) was arranged with the adhesive surface uppermost.

The dressings (10 cm×10 cm) prepared by example 2 or 3 was placed in the centre of the film.

A sheet of release paper (14 cm×14 cm) was placed over the complete dressing and the tackified polyurethane sheet.

EXAMPLE 5

A test method was developed using the TGA to determine the mass of dopant absorbed onto the surface of each of the following materials—charcoal cloth, a commercially available sodium alginate fabric bonded to activated charcoal cloth (suitably available under the trade mark KALTOCARB) and herein after referred to as alginate/charcoal fabric, a commercially available calcium sodium alginate (suitably available under the trade mark KALTOSTAT), a high absorbent alginate fabric having an absorbency of at least 40.0 grams of deionised water per gram of fabric and prepared as hereinbefore described and hereinafter referred to as SA fabric, and three alginate fabrics having particulate charcoal dispersed therein according to the present invention (hereinafter referred to as SA charcoal comp 1, 2 and 3).

The charcoal content of each of the materials was determined by dissolving a portion of each in a 10% EDTA solution and filtering to extract the charcoal.

The surfaces of each material were prepared by exposure to vacuum at room temperature for 5 minutes then placed above the desired dopant vapour for 30 minutes at RTP. The dopant species and the physical properties are given below in Table 1.

TABLE 1

| Dopant | R.M.M. | Melting Point | Boiling Point |
|---|---|---|---|
| Ammonia | 17.03 | −78° C. | −33° C. |
| Ethyl amine | 45.09 | −81° C. | 16.6° C. |
| Butyric acid | 88.11 | −7° C. to −5° C. | 162° C. |
| Ethyl acetate | 88.11 | −84° C. | 76.5° C. to 77.5° C. |
| Chloroform | 119.38 | −63° C. | 60.5° C. to 61.5° C. |

The above dopants were chosen in order to investigate the absorption of molecules of varying molecular weight, charge, melting and boiling points.

For each of the dressing materials the total number of moles of each dopant absorbed was calculated. This was then divided between the fraction absorbed by the alginate and that absorbed by the charcoal. The charcoal fraction was then scaled to assume 100% charcoal and also that the initial absorbency was only due to the charcoal component.

| Material | Ammonia | Ethyl Amine | Butyric Acid | Acetate Ethyl | Chloroform |
|---|---|---|---|---|---|
| Charcoal Cloth | | | | | |
| Total absorption | 0.868 | 0.301 | 0.089 | 0.160 | 0.185 |
| Alginate Component 0% | 0 | 0 | 0 | 0 | 0 |
| Charcoal component 100% | 0.868 | 0.301 | 0.089 | 0.160 | 0.185 |
| Charcoal component scaled to 100% charcoal | 0.868 | 0.301 | 0.089 | 0.160 | 0.185 |
| Total absorption scaled to 100% charcoal | 0.868 | 0.301 | 0.089 | 0.160 | 0.185 |
| Calcium Sodium Alginate | | | | | |
| Total absorption | 0.573 | 0.239 | 0.113 | 0.173 | 0.120 |
| Alginate Component 100% | 0.573 | 0.230 | 0.113 | 0.173 | 0.120 |
| Charcoal component 0% | 0 | 0 | 0 | 0 | 0 |
| Charcoal component scaled to 100% charcoal | 0 | 0 | 0 | 0 | 0 |
| Total absorption scaled to 100% charcoal | 0 | 0 | 0 | 0 | 0 |
| Alginate/Charcoal Fabric | | | | | |
| Total absorption | 0.713 | 0.177 | 0.077 | 0.130 | 0.088 |
| Alginate Component 25% | 0.143 | 0.060 | 0.028 | 0.043 | 0.030 |
| Charcoal component 48% | 0.569 | 0.117 | 0.049 | 0.087 | 0.058 |
| Charcoal component scaled to 100% charcoal | 1.185 | 0.244 | 0.102 | 0.181 | 0.121 |
| Total absorption scaled to 100% charcoal | 1.485 | 0.369 | 0.160 | 0.271 | 0.183 |
| SA Fabric | | | | | |
| Total absorption | 0.520 | 0.234 | 0.095 | 0.067 | 0.048 |
| Alginate Component 100% | 0.520 | 0.234 | 0.095 | 0.067 | 0.048 |
| Charcoal component 0% | 0 | 0 | 0 | 0 | 0 |
| Charcoal component scaled to 100% charcoal | 0 | 0 | 0 | 0 | 0 |
| Total absorption scaled to 100% charcoal | 0 | 0 | 0 | 0 | 0 |
| SA Charcoal Comp 1 | | | | | |
| Total absorption | 0.984 | 0.294 | 0.066 | 0.146 | 0.155 |
| Alginate Component 18% | 0.406 | 0.183 | 0.074 | 0.052 | 0.037 |
| Charcoal component 22% | 0.578 | 0.112 | — | 0.094 | 0.118 |
| Charcoal component scaled to 100% charcoal | 2.627 | 0.509 | — | 0.427 | 0.536 |
| Total absorption scaled to 100% charcoal | 4.473 | 1.336 | 0.300 | 0.664 | 0.705 |
| SA Charcoal Comp 2 | | | | | |
| Total absorption | 0.425 | 0.247 | 0.092 | 0.082 | 0.058 |
| Alginate Component 98% | 0.478 | 0.215 | 0.215 | 0.061 | 0.044 |
| Charcoal component 8% | — | 0.032 | 0.032 | −.020 | 0.014 |
| Charcoal component scaled to 100% charcoal | — | 0.400 | 0.400 | 0.250 | 0.175 |
| Total absorption scaled to 100% charcoal | 5.313 | 3.088 | 3.088 | 1.025 | 0.725 |
| SA Charcoal Comp 3 | | | | | |
| Total absorption | 0.568 | 0.253 | 0.102 | 0.093 | 0.091 |
| Alginate Component 0% | 0.432 | 0.194 | 0.079 | 0.055 | 0.040 |
| Charcoal component 100% | 0.136 | 0.059 | 0.023 | 0.037 | 0.051 |
| Charcoal component scaled to 100% charcoal | 0.800 | 0.347 | 0.135 | 0.218 | 0.300 |
| Total absorption scaled to 100% charcoal | 3.341 | 1.488 | 0.600 | 0.547 | 0.535 |

It can be seen from the above results by comparing the values obtained for total absorption scaled to 100% charcoal that the fabrics according to the present invention exhibited superior absorptive properties.

EXAMPLE 6

The resulting pad obtained by Example 1 was approximately 1 mm thick and was trimmed to 5×5 cm. The pad was placed in a bacteria proof pouch which was sealed and sterilized by irradiation (for example by gamma irradiation).

The wound dressings encompassed by the invention may comprise one or more of the wound dressing components well known in the art. For example, the wound dressing may comprise one or more adhesive layers. The wound dressing may also comprise one or more absorbent layers in addition to the alginate fabrics of the invention. The wound dressing may also comprise a separate and discrete layer which faces the wound.

EXAMPLE 7

Tan δ values were measured according to Test Method 2 above for a range of fibre samples the results were as follows:

| Fibre | Peak 1 Hz | Peak 2 Hz | Peak 3 Hz |
|---|---|---|---|
| KALTOSTAT[1] | 6449 | 1000 | 896 |
| KALTOGEL[2] | 578 | 416 | 46 |
| KALTOSTAT acid treated, neutralised and dried. | 2929 | 541 | 54 |
| Fibre prepared as in Example 1, charcoal treatment omitted. | 0.056 | 0.018 | — |
| As above, treated with calcium ions[3] | 5.412 | 2.928 | 0.464 |
| Fibre prepared as in Example 1. | 0.454 | 0.010 | 0.040 |

[1] commercially available calcium sodium alginate of high guluronate content
[2] commercially available calcium sodium alginate of high malluronate content
[3] the treatment comprised washing the fibres with three 2M $CaCl_2$ solutions each 200 ml per 1.5 g of fibre followed by washing three times with 200 ml of deionised water.

We claim:

1. An alginate fabric having particulate charcoal dispersed therein and comprising alginate fibres having an absorbency of at least 40 g of deionized water per gram of fabric.

2. An alginate fabric as claimed in claim 1 wherein the fabric is 0.5 mm to 5 mm thick.

3. An alginate fabric as claimed in claim 1 wherein the particulate charcoal is in the form of granules or powder.

4. An alginate fabric as claimed in claim 1 wherein the particulate charcoal is in the form of powder with a surface area of from 500 $m^2/g$ to 3000 $m^2/g$.

5. An alginate fabric as claimed in claim 1 wherein the charcoal comprises from 1% to 30% by weight of the fabric.

6. An alginate fabric as claimed in claim 1 wherein the fabric comprises alginate fibres which are characterised by having a split maxima in the range of 100° C. to 400° C. in a plot of the first order derivative of percentage weight loss of the fibre with temperature against temperature.

7. An alginate fabric as claimed in claim 1 wherein the fabric comprises fibres which are characterised by having two maxima in the range of 100° C. to 400° C. in a plot of the first order derivative of percentage weight loss of the fibre with temperature against temperature.

8. An alginate fabric as claimed in claim 1 wherein the fabric comprises alginate fibres obtainable by a process comprising the following steps:

i treating alginate fibres with suitable acid so as to produce fibres comprising approximately 90 to 98% alginic acid fibres;

ii treating the alginic acid fibres with a saturated aqueous solution of mono- or divalent cations;

iii washing the fibres with water until imbibition of water by the fibres has effectively ceased; and iv treating the fibres with a source of a cation capable of forming a water-soluble alginate salt.

9. An alginate fabric as claimed in claim 8 wherein the alginate fibres obtained in step i are calcium alginate.

10. An alginate fabric as claimed in claim 8 wherein other ions and/or medicaments are included after or during step iv.

11. An alginate fabric as claimed in claim 8 wherein the fibres comprise hyaluronic acid or a pharmaceutically acceptable salt thereof.

12. An alginate fabric as claimed in claim 1 comprising alginate fibres wherein the fibres are characterised by having a glass transition range of less than 30° C.

13. An alginate fabric as claimed in claim 1 comprising alginate fibres wherein the fibres are characterised by having a Tan δ value in the range from 0 to 15 Hz.

14. A wound dressing comprising an alginate fabric as claimed in claim 1.

15. A wound dressing comprising an alginate fabric as claimed in claim 1 in the form of a sterile dressing for the treatment of a burn or ulcer or other exuding wound.

* * * * *